US006548469B2

(12) United States Patent
Jalalian et al.

(10) Patent No.: US 6,548,469 B2
(45) Date of Patent: Apr. 15, 2003

(54) CLEANING COMPOSITIONS

(75) Inventors: Mohammad Jalalian, Darmstadt (DE); Maria Elisabeth Prenzel, Biebesheim (DE); Roland Martin, Weinheim (DE); Francesc Rosell I Oller, Barcelona (ES)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 10/166,179

(22) Filed: Jun. 11, 2002

(65) Prior Publication Data

US 2002/0183234 A1 Dec. 5, 2002

Related U.S. Application Data

(63) Continuation of application No. 09/284,132, filed as application No. PCT/EP97/05525 on Oct. 8, 1997.

(30) Foreign Application Priority Data

Oct. 17, 1996 (DE) .......................................... 196 42 957

(51) Int. Cl.[7] ................................................. C11D 9/42
(52) U.S. Cl. ........................ 510/370; 510/371; 510/372; 510/375; 510/379; 510/382; 510/383; 510/499; 514/546; 514/551; 514/919; 424/405; 424/DIG. 10; 134/42
(58) Field of Search ................................ 510/370, 371, 510/372, 375, 379, 382, 383, 499; 514/546, 551, 919; 424/405, DIG. 10; 134/42

(56) References Cited

U.S. PATENT DOCUMENTS

| 4,127,672 A | 11/1978 | Klier et al. | 424/311 |
| 4,965,286 A | 10/1990 | Krueger et al. | 514/514 |
| 6,306,905 B1 * | 10/2001 | Kurz et al. | 514/551 |
| 6,365,561 B1 * | 4/2002 | Vinson et al. | 510/235 |

FOREIGN PATENT DOCUMENTS

| AU | 15060/83 | 12/1983 |
| EP | 097813 | 1/1984 |
| EP | 346709 | 12/1989 |
| EP | 619363 | 10/1994 |

OTHER PUBLICATIONS

Xavier Belles et al. "Repellent Activity Different Formulations on the Domestic Cockroach *Blattella Germanica*", Jul. 1999.

"Household Cleaners with IR88" Report #7044, Universitat Autonoma Barcelona, Merck (1996).

"Bad News for Insects", *New Efficacy of Insect Repellent 88*, Merck (1997).

* cited by examiner

*Primary Examiner*—Gregory Delcotto
(74) *Attorney, Agent, or Firm*—Millen, White, Zelano & Branigan, P.C.

(57) ABSTRACT

The present invention relates to cleaning compositions which comprise the insect repellent ethyl 3-(N-butylacetamino)propionate and the use of this insect repellent in all types of cleaning compositions for repelling insects. This invention furthermore relates to a method for cleaning and for simultaneously repelling insects in which cleaning compositions comprising ethyl 3-(N-butylacetamino)propionate are used.

11 Claims, No Drawings

CLEANING COMPOSITIONS

This application is a continuation of U.S. application Ser. No. 09/284,132, filed Apr. 13, 1999, which was the National Stage of International Application No. PCT/EP97/05525, filed Oct. 8, 1997.

The invention relates to all types of cleaning compositions which comprise the insect repellent ethyl 3-(N-butylacetamino)propionate and are therefore used for cleaning and for simultaneously repelling insects from the surfaces and rooms to be cleaned.

In many respects, insects are a nuisance or even a threat to humans. In addition to the damage caused by some species of insects (for example the destruction of entire harvests), both humans and also many animals are troubled in one way or another, bitten and otherwise plagued by a wide range of insects. This can lead to infections and the transmission of dangerous diseases.

Insecticides are the main weapon in the fight against insects, but their use and toxicity profiles are not always without problems. These toxins often have undesirable effects on humans and animals, so that their use is limited or even banned.

However, measures such as the use of insecticides are not absolutely necessary to prevent the immediate nuisance. Some insects, such as, for example, cockroaches, in any case cannot be eradicated completely, and efforts are therefore increasingly directed more at repelling these insects than at destroying them.

Furthermore, protection of the environment is nowadays very much in the foreground, and preventive measures are therefore preferably taken.

Insect repellents are therefore now preferred to insecticides in combating insects, since the former are directed merely towards stopping insects from remaining and nesting on certain surfaces or in rooms.

Chemicals for repelling or destroying, for example, cockroaches, flies, mosquitoes or ants have been on the market for a long time, but many are dangerous to humans and animals or have a very unpleasant smell, so their adverse properties severely limit their use.

In view of the relatively small number of insect repellents which are not only effective but also acceptable from the toxicological aspect, great efforts to provide suitable products continue to be made in this field.

The object of the present invention was therefore to provide an insect repellent which effectively keeps away all types of insects, is easy to use and is toxicologically acceptable to humans and pets.

The substance ethyl 3-(N-butylacetamino)propionate is a proven insect repellent which has been known for a long time and is also employed as such in cosmetics formulations. It can be obtained commercially, for example from Merck KGaA, Darmstadt.

This substance, with its outstanding properties in respect of skin and mucosa tolerance without toxic, allergizing or sensitizing properties, has hitherto been used in cosmetics formulations in order to protect humans directly from attack by, for example, mosquitoes or flies.

This substance furthermore has a high chemical stability, i.e. it cannot be hydrolysed, cannot be photooxidized, cannot be oxidized and has a high heat stability.

Surprisingly, it has now been found that ethyl 3-(N-butylacetamino)propionate can also be incorporated into formulations of cleaning compositions of all types, and can therefore be used to drive off and keep away insects permanently from the surfaces cleaned with them, which can be hard or soft in nature.

It is known from the literature (U.S. Pat. No. 3,018,217), for example, to incorporate an insect repellent into a polishing composition for domestic floors, dibutyl succinate having been employed as the repellent. EP 0 525 893 also describes compositions for cleaning comprising various insect repellents, such as, for example, N,N-diethyl-m-toluamide (DEET). However, nowhere are cleaning compositions which comprise the abovementioned ethyl 3-(N-butylacetamino)propionate described.

In contrast to the prior art, the invention employs an insect repellent which has hitherto been used directly on humans, and the cleaning compositions according to the invention can thus be regarded as toxicologically acceptable and are therefore highly superior to the compositions known to date.

The term "insect" is used here in the broadest sense and is intended to include, for example, common cockroaches (German cockroaches and also American roaches), fleas, flies, mosquitoes, ants, lice, ticks, bugs and even spiders.

The invention thus relates to a cleaning composition which is characterized in that it comprises an active amount, which is sufficient to repel insects after treatment with this cleaning composition, of the insect repellent ethyl 3-(N-butylacetamino)propionate.

The invention furthermore relates to the use of the insect repellent ethyl 3-(N-butylacetamino)propionate in cleaning compositions for repelling insects.

The invention furthermore relates to a process for cleaning and simultaneously repelling insects, which is characterized in that a cleaning composition comprising an active amount, which is sufficient to repel insects, of the insect repellent ethyl 3-(N-butylacetamino)propionate is used on the surfaces to be cleaned.

The cleaning compositions according to the invention preferably comprise 0.1 to 20% by weight of ethyl 3-(N-butylacetamino)propionate, particularly preferably 0.1 to 10% by weight, especially preferably 0.1 to 6% by weight.

The insect repellent of the present invention can be incorporated into all types of cleaning compositions, preferably into domestic cleaners. If appropriate, these domestic cleaners can additionally comprise, as well as the ethyl 3-(N-butylacetamino)propionate according to the invention, one or more insect repellents in each case in an amount of 0.1 to 20% by weight. These can be both synthetic substances, such as, for example, diethyltoluamide, 2-ethyl-1,3-hexanediol, dimethyl phthalate or dibutyl succinate, and also essential oils which are naturally occurring or identical to those in nature and act as insect repellents, such as, for example, menthol oil, citronella oil or lemon oil.

The insect repellent is preferably incorporated into solutions (aqueous or aqueous-alcoholic) or dispersions (or dispersed in a pulverulent carrier), into cleaning agent compositions such as detergents, floor or wall cleaners (tile cleaners), window cleaners, upholstery or carpet cleaners, also in shampoo form, into solid or liquid soaps, into wax, into creams or into sprays.

It can be incorporated into any other suitable formulation in which it could be of benefit, for example into insecticides or antibacterial compositions, furniture polishes or, floor waxes or else into compositions for cleaning certain hand tools which are used, for example, for animal husbandry or in horticulture.

The use of the cleaning compositions according to the invention causes insects to avoid contact with the cleaned surface after the hard or soft surfaces have been cleaned, since a film of this cleaning composition comprising the insect repellent has been formed as a result of the cleaning process.

The insects are additionally kept away from the area of the cleaned surface by the smell of this composition.

Thus, for example, ants, common cockroaches and other insects can be stopped from penetrating into storage rooms by cleaning shelves, walls and the floor with a cleaning composition according to the invention.

Cleaning upholstery or carpets with suitable shampoos can also stop the insects from nesting there and laying their eggs therein.

Detergents can furthermore prevent insects from entering linen cupboards and therefore into clothes.

From the above description, it is obvious that a wide range of compositions are possible for the cleaning agent according to the invention, and the cleaning compositions can be used for many different purposes.

However, the invention is preferably used in the field of domestic cleaners.

Such cleaners are composed of a large number of components.

For example, they comprise organic (soaps) or preferably synthetically organic surface-active, wash-active substances (surfactants), which can be anionic, amphoteric, ampholytic, zwitterionic, nonionic or cationic in nature, or else a mixture thereof. The anionic detergent bases are by far the most important here. Many such detergents are described in "Surface Active Agents and Detergent", Volume II, by Schwartz, Perry and Berch (1958 Interscience Publishers, Inc.). However, the expert can also read about the most common surfactants in all the major reference works of chemistry (for example Römpp, Beilstein and the like).

The cleaners furthermore comprise builders and, if appropriate, bleaching agents, fragrances and auxiliaries.

Any detergent suitable for this purpose can be used as an anionic surfactant. Anion-based surfactants usually include, for example, fatty alcohol sulfates, paraffinsulfonates, fatty acid condensation products and alkylbenzenesulfonates and -phosphonates, and also alkyl sulfates and phosphates. The anionic surfactants are preferably sodium salts, but potassium, ammonium and triethanolammonium salts are also often employed in some liquid compositions. The alkyl radicals are preferably straight-chain and preferably have 12 to 16 carbon atoms.

Synergistic combinations, primarily with fatty alcohol polyglycol ethers, have proved suitable as the base for many compositions.

Suitable nonionic raw materials are condensation products of lipophilic components and lower alkylene oxides or polyalkyleneoxy units. The fatty alcohol polyglycol ethers mentioned, the alkylphenol polyglycol ethers or else fatty acid alkylamides, for example, are preferably employed.

Cationic surfactants can also be used, for example aliphatic quaternary ammonium salts.

The substances known as builders are also generally known and can be inorganic or organic in nature and water-soluble or insoluble. Substances such as polyphosphates, for example pentasodium triphosphate, carbonates or bicarbonates, for example sodium carbonate or sodium bicarbonate, zeolites, for example zeolite A, polycarboxylates, for example sodium salts of copolymers of acrylic acid and maleic acid, and also borates and silicates, for example laminar sodium silicate, are preferred.

Further auxiliaries or additives which can be added are fragrances and dyestuffs, bleaching agents or brighteners, antistatic agents, antibacterial agents, fungicides, foam-forming reagents and also anti-foaming substances, antioxidants and enzymes.

The abovementioned substances for composing cleaning compositions are intended to be examples and have no limiting character for the formulations according to the invention.

All the substances known in the prior art which are described for formulating such cleaning compositions can be mixed according to the invention with ethyl 3-(N-butylacetamino)propionate.

The cleaning compositions according to the invention can be present in solid form, as a powder, as tablets, in block or piece form, as a paste, as a gel, in liquid form, as a wax, as a cream, as an emulsion, as a dispersion, as a foam or as a spray (aerosol form) or as other suitable forms appropriate for the particular use.

The quantitative composition of the individual components for the various formulation possibilities is well-known to the expert in this field and does not have to be listed here in more detail.

According to the invention, the content of ethyl 3-(N-butylacetamino)propionate in the particular formulations is 0.1 to 20% by weight, preferably 0.1 to 10% by weight, especially preferably 0.1 to 6% by weight.

The cleaning compositions according to the invention are preferably present as an aqueous or aqueous-alcoholic solution, as a detergent, as a wax, as a gel, as an emulsion, as a cream, as a shampoo, as a spray, as a dispersion or as a solid product.

The methods for the preparation of such products are generally known to the expert in the field of preparation of soaps and detergents and do not have to be explained in more detail here.

To prepare an aqueous or aqueous-alcoholic solution, the insect repellent is preferably dissolved in a suitable solvent, such as water (which usually means demineralized water), lower alcohols, such as, for example, ethanol, or mixtures thereof. These mixtures can of course also additionally comprise other substances, such as, for example, esters, aldehydes, ketones, hydrocarbons and also halogenated hydrocarbons. Examples of the latter which may be mentioned are isobutane, dichlorodifluoromethane, monofluorotrichloromethane and other chlorinated and/or fluorinated methanes, ethanes or propanes. Such substances include those liquefiable gases which remain in the liquid state in pressurized containers ready for use as sprays.

Particularly preferred cleaning compositions of this invention comprise, as a synthetic organic surfactant, an anionic or nonionic surfactant, or mixtures thereof, builders and/or fillers and the insect repellent.

These cleaning compositions or detergents can be present in particle form or in liquid form. The liquid form comprises the same individual components, but in addition a liquid medium, and if appropriate also emulsifying substances and other auxiliaries.

Preferred shampoos for cleaning upholstery or carpets also comprise water-soluble soaps and synthetic wash-active substances, builder salts, the insect repellents, and usually water as the liquid medium. Such shampoos can also be formulated as a gel or in paste or powder form.

Solid products according to the invention in block, tablet or piece form (bars of soap), which can be used for cleaning laundry, carpets and/or hard surfaces, such as, for example, floors and walls, can also be prepared.

In all these formulations, the ratios of soaps or synthetic organic surfactants, builders and auxiliaries to insect repellent are similar and can be varied within wide ranges. Preferably, the formulations comprise 1 to 40% of surfactants or soaps, 10 to 90% of builders and fillers and 0.1 to 20% of ethyl 3-(N-butylacetamino)propionate (figures in % by weight). Water, alcohols, auxiliaries and/or emulsifying substances are usually added for completion (to 100% by weight).

The various cleaning compositions described can be prepared by methods known to the expert. Such processes include spray drying, dry mixing, dissolving and/or dispersing and/or emulsifying, grinding or alternatively pressing.

When the cleaning compositions according to the invention are applied by spraying, wiping, rubbing or other methods to the surfaces to be cleaned, the insect repellent which they comprise is deposited on these surfaces in a sufficiently high concentration or amount to act as a repellent against insects.

Particularly preferred cleaning compositions of this invention are those in liquid form.

The following formulations, which are used as general-purpose cleaners, are especially preferred embodiments according to the invention.

Amphoteric surfactants, for example those based on cocamidoalkylbetaine, alone or mixed with anionic, cationic and nonionic surfactants, are preferably employed in these general-purpose cleaners. Neutral formulations as well as alkaline or acidic compositions can be prepared with these.

Salt-free capryl iminodipropionate is preferably employed as a further amphoteric surfactant for use in highly alkaline or strongly acidic formulations.

Further particularly preferred surfactant groups are the amine oxides and the alkyl poly-glucosides, which are particularly readily mixed with betaines and lauryl ether sulfates.

General-purpose cleaners can be employed universally, as the name implies. They are usually neutral to slightly alkaline formulations.

Formulations according to the invention of this type with antibacterial additives are also particularly preferred.

The cleaning compositions according to the invention have a particularly good action against ants and common cockroaches.

With the cleaning compositions of the present invention, the consumer thus has available essentially non-toxic and therefore highly environment-friendly but nevertheless highly active products.

By using the cleaning compositions according to the invention and the process according to the invention, it has been possible to demonstrate in practice that, for example, significantly fewer cockroaches were to be found behind cupboards or under refrigerators compared with beforehand.

If floors, walls, sinks, doors or cupboards in a house or flat are therefore treated regularly with the cleaning compositions according to the invention, the incidence of insects, in particular cockroaches or ants, is reduced practically to zero.

Without further embodiments, it is also assumed that an expert can use the above description in the broadest scope. The preferred embodiments are therefore to be interpreted merely as a descriptive and not in any way as a limiting disclosure.

The complete disclosure of all the Applications, Patents and publications mentioned above and below is introduced into this Application by reference.

The following examples are intended to illustrate the invention.

EXAMPLE 1

General-Purpose Cleaner with a Good Cleaning and Insect Repellent Action

Composition:

|  |  | % |
|---|---|---|
| Ethyl 3-(N-butylacetamino) propionate (Art. No. 111887) | (1) | 3.000 |
| Teqo ® Betaine F 50 | (2) | 7.500 |
| Ammonyx LO | (2) | 10.000 |
| Texapon N 28 | (3) | 15.000 |
| Trisodium citrate dihydrate (Art. No. 106446) | (1) | 4.000 |
| Sodium carbonate (Art. No. 106392) | (1) | 3.000 |
| Ethanol 96% (Art. No. 100971) | (1) | 3.000 |
| Water, demineralized |  | to 100.000 |

The sodium carbonate and trisodium citrate are dissolved in water. The other substituents are then added in the sequence shown while stirring.

Sources of Supply:
Merck KGaA, Darmstadt
Th. Goldschmidt AG, Essen
Henkel KGaA, Düsseldorf

EXAMPLE 2

Alkaline General-Purpose Cleaner

Composition:

|  |  | % |
|---|---|---|
| Ethyl 3-(N-butylacetamino) propionate (Art. No. 111887) | (1) | 3.000 |
| Tegotain ® 485 | (2) | 10.000 |
| Lutensol A 8 | (3) | 9.000 |
| Trisodium citrate dihydrate (Art. No. 106446) | (1) | 3.000 |
| Water, demineralized |  | to 100.000 |

The trisodium citrate is dissolved in water. The other constituents are then added in the sequence shown while stirring.

Sources of Supply:
Merck KGaA, Darmstadt
Th. Goldschmidt AG, Essen
BASF, Ludwigshafen

EXAMPLE 3

Antibacterial General-Purpose Cleaner

|  |  | % |
|---|---|---|
| Ethyl 3-(N-butylacetamino) propionate (Art. No. 111887) | (1) | 3.000 |
| Teqo ® Betaine F 50 | (2) | 5.000 |
| BTC 50 | (2) | 5.000 |
| Trisodium citrate dihydrate (Art. No. 106446) | (1) | 4.000 |
| Sodium carbonate (Art. No. 106392) | (1) | 3.000 |
| Water, demineralized |  | to 100.000 |

The sodium carbonate and trisodium citrate are dissolved in water. The other constituents are then added in the sequence shown while stirring. An antibacterially acting general-purpose cleaner with an insect-repellent action is obtained.

Sources of Supply:

Merck KGaA, Darmstadt

Th. Goldschmidt AG, Essen

What is claimed is:

1. A method of cleaning a surface and repelling cockroaches and ants from said surface, said method comprising applying a cleaning composition to said surface wherein said cleaning composition is based on an aqueous or aqueous-alcoholic solution or which is in the form of a detergent, wax, gel, shampoo, spray, solid product, emulsion, cream or dispersion, wherein said cleaning composition comprises:

one or more surfactants;

one or more builders;

an amount of the insect repellent ethyl 3-(N-butylacetamino)propionate effective to repel cockroaches and/or ants;

one or more bleaching agents;

optionally a liquid medium; and optionally one or more fragrances, one or more dyestuffs, or brighteners, one or more antistatic agents, one or more antibacterial agents, one or more fungicides, one or more foam-forming agents, one or more anti-foaming agents, one or more antioxidants, one or more enzymes, or combinations thereof.

2. A method according to claim 1, wherein said cleaning composition comprises 0.1 to 20% by weight of ethyl 3-(N-butyl-acetamino) propionate and, optionally, one or more additional insect repellents in an amount of 0.1 to 20% by weight.

3. A method according to claim 1, wherein said cleaning composition further comprises one or more insect repellents selected from the group consisting of diethyltoluamide, 2-ethyl-1,3-hexanediol, dimethyl phthalate, dibutyl succinate, one or more essential oils, or combinations thereof, which act as insect repellents.

4. A method according to claim 1, wherein said cleaning composition further comprises one or more essential oils which act as insect repellents selected from the group consisting of citronella oil, menthol oil and lemon oil.

5. A method according to claim 1, wherein said cleaning composition comprises 0.1 to 20% by weight of ethyl 3-(N-butyl-acetamino) propionate, and one or more additional insect repellents in an amount of 0.1 to 20% by weight.

6. A method according to claim 5, wherein said additional insect repellant is diethyltoluamide, 2-ethyl-1,3-hexanediol, dimethyl phthalate, dibutyl succinate, one or more essential oils, or combinations thereof.

7. A method according to claim 1, wherein said cleaning composition comprises:

1–40 wt. % of at least one surfactant or soap,

10–90% of at least one builder or filler, and 0.1–20% of ethyl 3-(N-butylacetamino) propionate.

8. A method according to claim 1, wherein said one or more surfactants are selected from anionic surfactants, nonionic surfactants, and combinations thereof.

9. A method according to claims 8, wherein said composition contains a liquid medium.

10. A method according to claim 9, wherein said composition contains one or more fragrances, one or more dyestuffs, one or more bleaching agents or brighteners, one or more antistatic agents, one or more antibacterial agents, one or more fungicides, one or more foam-forming agents, one or more anti-foaming agents, one or more antioxidants, one or more enzymes, or combinations thereof.

11. A cleaning composition for cleaning surfaces and repelling cockroaches and/or ants, said cleaning composition comprising:

one or more surfactants;

one or more builders;

an amount of the insect repellent ethyl 3-(N-butylacetamino)propionate effective to repel cockroaches and/or ants;

one or more bleaching agents;

optionally a liquid medium; and optionally one or more fragrances, one or more dyestuffs, or brighteners, one or more antistatic agents, one or more antibacterial agents, one or more fungicides, one or more foam-forming agents, one or more anti-foaming agents, one or more antioxidants, one or more enzymes, or combinations thereof.

* * * * *